United States Patent [19]

Perlin

[11] Patent Number: 4,556,060
[45] Date of Patent: Dec. 3, 1985

[54] SURGICAL CLIP

[75] Inventor: Alfred R. Perlin, Highland Park, Ill.

[73] Assignee: Metatech Corporation, Northbrook, Ill.

[21] Appl. No.: 429,170

[22] Filed: Sep. 30, 1982

[51] Int. Cl.$^4$ ............................................. A61B 17/12
[52] U.S. Cl. .................................... 128/325; 128/346; 24/552
[58] Field of Search ............... 128/325, 322, 346, 321, 128/354; 24/551, 552, 499

[56] References Cited

U.S. PATENT DOCUMENTS

| | | | |
|---|---|---|---|
| 1,837,277 | 12/1931 | Lund | 128/321 |
| 2,215,725 | 9/1940 | Martinson | 128/346 |
| 2,583,020 | 1/1952 | Smith | 24/551 |
| 3,061,263 | 10/1962 | Butler | 128/346 X |
| 3,392,727 | 7/1968 | Hanlon | 128/354 |
| 3,446,211 | 5/1969 | Markham | 128/322 |
| 3,996,937 | 12/1976 | Williams | 128/346 X |
| 4,360,023 | 11/1982 | Sugita et al. | 128/325 |

Primary Examiner—Michael H. Thaler
Attorney, Agent, or Firm—James B. Raden

[57] ABSTRACT

A surgical clip comprises a body with two outwardly projecting jaws. The body includes a passage through which one of the jaws is inserted to form a looped body with the jaws extending outwardly in mutually juxtaposed relationship. The body is integrally hinged at its midsection. The jaws are formed to provide a reverse curve clamping path for an interposed member such as a blood vessel and, in a preferred embodiment, a trough for supporting the member is formed in one of the jaws.

10 Claims, 9 Drawing Figures

U.S. Patent     Dec. 3, 1985     4,556,060
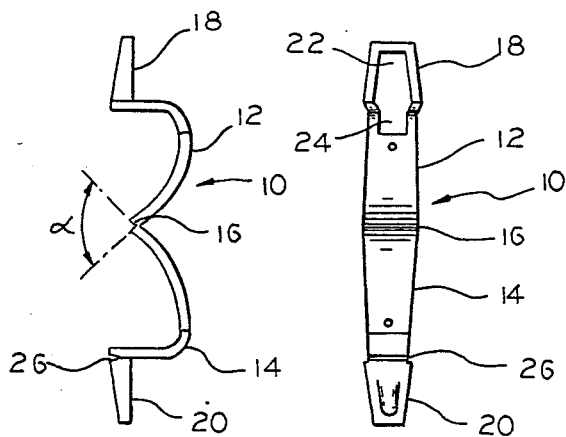
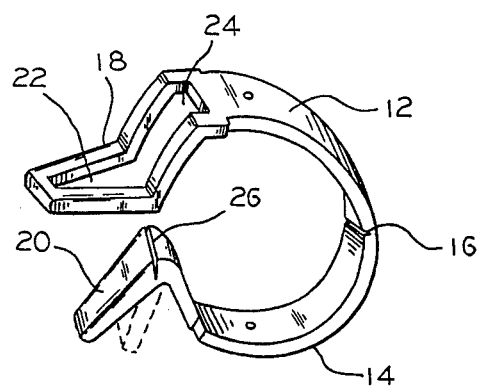
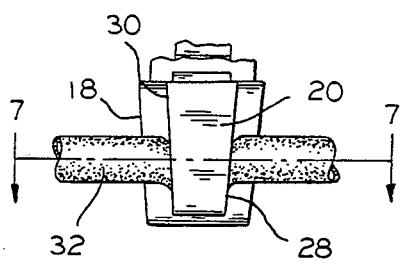
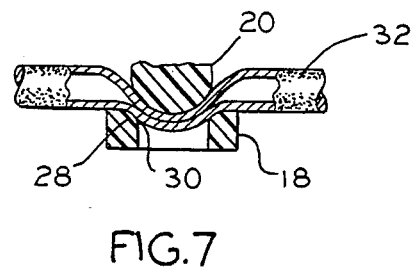
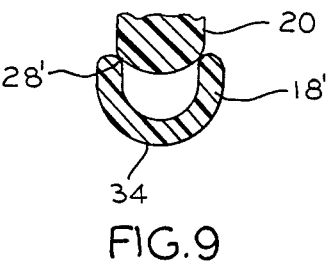

SURGICAL CLIP

BACKGROUND OF THE INVENTION

This invention relates generally to surgical clips and, more particularly, to clips for temporarily occluding blood vessels during surgery.

A wide variety of surgical clips have been proposed heretofore for purposes of vascular occlusion. However, many of these clips have been constructed in a manner such that they directly squeeze or pinch the vessel closed between opposing and converging flat surfaces. The clamping action of these prior clips necessarily gives rise to the possibility of damage or rupture of the vessel as a result of their intrusive pinching or crushing effect on the clamped vessel. Other clips, as exemplified by the clips described in U.S. Pat. Nos. 3,996,937 and 4,024,868, have been constructed to avoid this pinching or crushing action on the vessel. However, those clips are designed to cause permanent occlusion and are not suitable for temporary occlusion in view of the closure action of the metallic rod-like clamping members which exert relatively high pressure on the clamped vessels and cause complete collapse of the vessel walls.

Thus, it has been a continuing problem in the design of surgical clips to develop a clip for the temporary occlusion of blood vessels which is effective in stopping blood flow without causing permanent occlusion or present risk of traumatic damage to the vessel.

A further problem which has been encountered with prior surgical clips is that they have been manufactured and stored in a stressed condition. Over a period of time, such devices lose their elasticity and upon application may not provide the necessary clamping force or pressure to occlude a vessel and, if sufficient pressure is not exerted, the potential exists for slippage or disengagement of the clip from the vessel.

SUMMARY OF THE INVENTION:

The present invention is directed to an improved surgical clip particularly adapted for the clamping of blood vessels. The clip preferably has a unitary body construction of a suitable springy material such as acetal, polyethylene, polypropylene or like plastic materials. The body includes first and second arms integrally hinged at one end and each arm terminates at its other end in an outwardly projecting clamping jaw.

In an unassembled state, the clip can be stored in an unstressed condition and can be readily assembled by inserting one of the jaws through a passage positioned in the opposite arm of the clip forming the arms essentially into a loop with the jaws extending outwardly therefrom in mutual juxtaposition. The jaws are thereby positioned to be opened to receive or remove a member such as a blood vessel as a result of movement of the arms and to be clampingly closed about the vessel in response to an opposite movement of the arms.

The jaws are formed and positioned to provide a reverse curve or S-shaped clamping path for the vessel so that occlusion of blood flow can be accomplished with minimal applied clamping force or pressure thereby reducing the potential for damage of the clamped vessel. With regard to the clamping force, it has been found that the force which the jaws of the present clip exert on a vessel is directly related to the angular configuration of the integral or living hinge which joins the arms. Thus, depending on the selection of the included angle of taper defining the integral or living hinge, the clamping force which the jaws will exert can be predetermined to provide an effective but not harmful degree of pressure for the temporary occlusion of a vessel. Ideally, this clamping force or pressure should approximate the systolic pressure in the vessel, normally in the range of about 100 to 300 mm Hg., in order to temporarily stop the flow of blood therein without causing potential damage to the vessel.

It is, therefore, an object of the invention to provide an improved surgical clip particularly adapted for clamping blood vessels.

It is a further object to provide a surgical clip adapted to be stored in an unstressed condition which can be readily assembled for use during surgery.

Another object is to provide a surgical clip which is effective for the occlusion of blood vessels but is not harmful to a clamped vessel.

A still further object is to provide a surgical clip which exerts a predetermined clamping force on a vessel sufficient to temporarily occlude the vessel without causing permanent occlusion thereof.

BRIEF DESCRIPTION OF THE DRAWINGS

The foregoing and other objects and advantages of this invention will become more readily appreciated as the same becomes completely understood by reference to the following detailed description when taken in conjunction with the accompanying drawings wherein:

FIG. 1 is a side elevational view of an unassembled surgical clip in accordance with the present invention;

FIG. 2 is a plan view of the surgical clip of FIG. 1;

FIG. 3 is a perspective view of the surgical clip of FIG. 1 in a partially assembled condition;

FIG. 4 is a side elevational view of the surgical clip of FIG. 1 in a fully assembled rest position;

FIG. 5 is a side elevational view of the surgical clip of FIG. 1 in a fully assembled open position to receive a vessel;

FIG. 6 is a plan of the jaws of the surgical clip of FIG. 1 in a closed position clamped on a vessel;

FIG. 7 is a cross-sectional view taken at line 7—7 of FIG. 6;

FIG. 8 is a partial perspective view of an alternate embodiment of a jaw of the surgical clip of FIG. 1; and FIG. 9 is a sectional view of the jaws of the surgical clip in a fully assembled rest position employing the jaw of FIG. 8.

DETAILED DESCRIPTION

Referring now to FIG. 1 and 2 there is shown generally at 10 an elongated surgical clip body in its fully open, unassembled, unstressed condition suitable for storage. The clip body 10 may be provided in a number of lengths and widths, however, the comparative shapes and relationship of components parts thereof are generally maintained. Clip 10 includes arms 12 and 14 which are hingedly joined by an integral or living hinge 16. Clamping jaws 18 and 20 are formed integral with and project outwardly from arms 12 and 14 respectively. The clip 10 including both arms 12 and 14 and jaws 18 and 20 preferably is molded as a unitary member of a springy material such as nylon or a suitable flexible but somewhat rigid plastic material such as acetal, polyethylene, polypropylene or the like.

The jaw 18 includes a longitudinally extending slot 22 which tapers inwardly lengthwise of jaw 18. Jaw 20 is cooperatively tapered longitudinally in a manner such that the jaws 18 and 20 are adapted to be nestingly engaged when clip 10 is assembled.

Assembly of clip 10 is readily accomplished by passing arm 14 and its associated jaw 20 through a passage 24 included in arm 12 thereby essentially forming arms 12 and 14 into a loop with jaws 18 and 20 extending outwardly therefrom in mutual juxtaposition as clearly shown in FIG. 4. In order to facilitate this assembly, undercut 26 may be provided, if desired, at the junction of arm 14 and jaw 20. This undercut 26 assists in cocking jaw 20 into a position as illustrated by dashed lines in FIG. 3 which is more easily adapted to be inserted through passage 24.

To further facilitate assembly of the clip 10, integral hinge 16 is provided. Hinge 16 is an integral or living hinge defined by a tapered, rounded or ridged undercut in the clip body 10 having an included angle $\alpha$ between the walls of the undercut when the clip 10 is in the fully open, unassembled state as shown in FIG. 1. Functionally, this hinge 16 makes it easier to move the clip 10 into position for assembly. Additionally, it should be noted that the angular configuration of the integral hinge 16 is of great importance in achieving the desired clamping force or pressure which jaws 18 and 20 will exert on a blood vessel clamped therebetween when clip 10 is fully assembled. It has been found that the clamping force which jaws 18 and 20 will exert is directly related to and may be predetermined by the selection of the angle $\alpha$. Thus, in a preferred embodiment of this surgical clip, angle $\alpha$ ranges from about 140° to about 170° in order to provide a clamping force approximating the normal systolic pressure in a blood vessel which is about 100 to about 300 mm Hg. Such clamping forces are preferred since they are sufficient to effectively retain the clip on the vessel without causing traumatic damage or lasting harmful effects thereof.

FIG. 5 illustrates clip 10 in a fully assembled open position to accommodate a blood vessel interposed between jaws 18 and 20. Opening of jaws 18 and 20 from their closed rest position as shown in FIG. 4 is accomplished by manually compressing arms 12 and 14 towards one another either by pressure exerted by fingers grasping clip 10 or by a delivery means with sufficient force to overcome the bias of the springy material which urges arms 12 and 14 apart and concomitantly the jaws 18 and 20 into the closed or rest condition. Thus, by overcoming the spring bias of the material of which the clip 10 is formed, the jaw 18 is urged downwardly and the jaw 20 is urged upwardly to provide an opening to accommodate a blood vessel interposed between the jaws 18 and 20. In order to clampingly engage the interposed vessel the compressive pressure on arms 12 and 14 is released and the aforementioned inherent bias will cause the jaws 18 and 20 to close in order to clamp or occlude vessel 32 in a manner shown in FIGS. 6 and 7.

When jaws 18 and 20 are in a fully assembled closed position, jaw 20 is disposed lengthwise of slot 22 and is substantially centered between lateral edges 28 of slot 22 with lateral edges 30 of jaw 20 abutting in nesting engagement with lateral edges 28. Preferably, the lateral edges 28 and 30 are conformably tapered or rounded and most preferably are elliptically shaped in cross-section, to provide this nesting engagement. Thus, as shown in FIGS. 6 and 7, when a blood vessel 32 is interposed between jaws 18 and 20, a reverse curve or S-shaped clamping path is provided for vessel 32 with the tapered or rounded edges 28 of slot 22 in conjunction with the conformably tapered or rounded edges 30 of jaw 20 applying a uniformly distributed pressure against the opposing lateral sides of the vessel 32 to accomplish occlusion thereof. It should be noted that in view of the tapered construction of edges 28 and 30 no sharp surfaces are in contact with vessel 32 as the clamping force is applied. Accordingly, the potential for damage or pinching of the vessel resulting from the application of the compressive force to occlude the vessel 32 is greatly diminished. Furthermore, as a result of the application of uniformly distributed pressure at a plurality of sealing points along the clamping path for vessel 32, the occlusive action of the jaws 18 and 20 can be accomplished with a minimum of pressure to achieve effective temporary stoppage of blood flow without causing permanent occlusion thereof.

In FIG. 8, an alternative embodiment of the jaw 18 is shown generally at 18'. In this embodiment of the jaw, a web or cradle 34 is formed to provide a trough for supporting an interposed vessel. The web 34 extends at least partially coextensive with the length of a slot 22' which corresponds to slot 22 described hereinbefore. The length of web 34 and the positioning thereof along the legnth of slot 22' is not critical so long as it is sufficient to accommodate the vessel being occluded by the clip. As illustrated in cross-section in FIG. 9, the jaw 18' and the hereinbefore described jaw 20 are shown in a fully assembled, rest position prior to the interposition and clamping of a vessel therebetween. It will be seen that the lateral edge of jaw 18' and the lateral eldge 28' of the slot 22' are conformably tapered and abut in nesting engagement. Thus, in operation, when the jaws 18' and 20 are moved into an open position, a vessel is inserted therebetween and will be supported by the web 34 as the jaws 18' and 20 are moved back together into a closed, clamping position about the vessel.

The forms of this invention illustrated and described herein are but preferred embodiments of these teachings in the forms currently preferred for manufacture. They are shown as illustrations of the inventive concepts, however, rather than by way of limitation, and it is pointed out that modifications and alterations may be indulged in within the scope of the appended claims.

I claim:

1. A surgical clip of unitary construction for the temporary clamping of blood vessels comprising first and second arms hingedly joined at one end, said first arm terminating at its other end in an outwardly projecting first clamping jaw and said second arm terminating at its other end in an outwardly projecting second clamping jaw, said first arm including a passage integral with said first arm and disposed therein through which said second arm is inserted to essentially form said arm into a loop and to position said first and second jaws in mutual juxtaposition, an undercut formed at the juncture of said second arm and said second jaw adapted to allow said second jaw to be cocked to facilitate insertion of said second arm through said passage, said mutually juxtaposed jaws being biased into engagement when said clip is in a rest position, said arms being formed of a springy material and being movable toward and away from each other whereby said jaws can be urged into an open position to accommodate a blood vessel interposed between said jaws or into a closed clamping position about said interposed blood vessel.

2. The clip of claim 1 wherein said first and second arms are hingedly joined by an integral hinge defined by an undercut formed at said one end.

3. The clip of claim 1 wherein said jaws exert a predetermined clamping force on a blood vessel interposed therebetween when said jaws are in said closed position, said predetermined force approximating the systolic pressure in said blood vessel.

4. The clip of claim 3 wherein said predetermined clamping force ranges from about 100 mm to about 300 mm Hg.

5. The clip of claim 1 wherein a longitudinally extending slot is formed in said first jaw to accommodate said second jaw, said second jaw being disposed lengthwise of said slot and substantially centrally of the lateral edges of said slot with the lateral edges of said second jaw abutting in nesting engagement with the lateral edges of the slot when said clip is in a rest position and whereby a reverse curve clamping path is provided for a vessel interposed between said jaws when said clip is in a closed clamping position.

6. The clip of claim 5 wherein said lateral edges of said slot and said lateral edges of said second jaw are conformably tapered to provide said nesting engagement of said jaws.

7. The clip of claim 6 wherein said conformably tapered edges of said slot and said second jaw are elliptical in cross-section.

8. The clip of claim 5 wherein a web is formed on a surface of said first jaw opposite said second jaw and at least partially coextensive with the length of said slot defining a trough to support said vessel as said clip is clampingly closed about said vessel.

9. A surgical clip of unitary construction comprising an elongated body terminating at both ends in outwardly projecting jaw members, a passage formed integral with and through said body adjacent a first one of said jaws adapted to receive the looped remote second jaw of the clip to essentially form a looped body with said jaws projecting outwardly therefrom in mutually juxtaposed relationship, said body being integrally hinged at its mid-section, said first jaw including a slot, said slot being a longitudinal extension of said passage, said slot and said second jaw being cooperatively tapered longitudinally whereby said slot is adapted to nestingly accommodate said second jaw and an undercut is formed at the juncture of said body and said remote jaw adapted to allow said remote jaw to be cocked whereby assembly of said clip is facilitated.

10. The clip of claim 9 including a web formed on said first jaw beneath said slot, said web defining a trough which extends at least partially coextensive with the length of said slot.

* * * * *